(12) United States Patent
Lee et al.

(10) Patent No.: US 12,102,839 B2
(45) Date of Patent: Oct. 1, 2024

(54) LED PATCH FOR SKIN CARE APPARATUS AND SKIN CARE APPARATUS INCLUDING THE SAME

(71) Applicant: AMOLIFESCIENCE CO., LTD., Seoul (KR)

(72) Inventors: Hyo Jung Lee, Seoul (KR); In Yong Seo, Seoul (KR); Seon Ho Jang, Seoul (KR)

(73) Assignee: AMOLIFESCIENCE CO., LTD., Seoul (KR)

( * ) Notice: Subject to any disclaimer, the term of this patent is extended or adjusted under 35 U.S.C. 154(b) by 121 days.

(21) Appl. No.: 17/614,758

(22) PCT Filed: May 22, 2020

(86) PCT No.: PCT/KR2020/006681
§ 371 (c)(1),
(2) Date: Nov. 29, 2021

(87) PCT Pub. No.: WO2020/242141
PCT Pub. Date: Dec. 3, 2020

(65) Prior Publication Data
US 2022/0226668 A1    Jul. 21, 2022

(30) Foreign Application Priority Data
May 30, 2019   (KR) .................. 10-2019-0063897

(51) Int. Cl.
*A61N 5/06*      (2006.01)
*A61M 37/00*   (2006.01)

(52) U.S. Cl.
CPC ........... *A61N 5/0616* (2013.01); *A61M 37/00* (2013.01); *A61N 5/0624* (2013.01);
(Continued)

(58) Field of Classification Search
CPC .. A61N 5/0616; A61N 5/0624; A61N 5/0625; A61N 2005/0645;
(Continued)

(56) References Cited

U.S. PATENT DOCUMENTS

2013/0226269 A1*  8/2013  Eckhouse ............ A61N 5/0616
                                                                    607/148
2018/0099143 A1   4/2018  Kim et al.
(Continued)

FOREIGN PATENT DOCUMENTS

KR    10-2011-0001704 A    1/2011
KR       101031908 B1       5/2011
(Continued)

OTHER PUBLICATIONS

International Search Report issued in PCT/KR2020/006681 dated Sep. 11, 2020, 2 pages.

*Primary Examiner* — Carl H Layno
*Assistant Examiner* — Aya Ziad Bakkar
(74) *Attorney, Agent, or Firm* — Rothwell, Figg, Ernst and Manbeck, P.C.

(57) ABSTRACT

An LED patch for a skin care apparatus is provided. An LED patch for a skin care apparatus according to an exemplary example of the present invention comprises: a substrate part; a circuit pattern part formed in at least two layers on the substrate part; a light source part including one or more LEDs mounted on one surface of the substrate part; and a cover part configured to cover at least one surface of the substrate part.

19 Claims, 15 Drawing Sheets

(52) U.S. Cl.
CPC ... *A61N 5/0625* (2013.01); *A61M 2037/0007* (2013.01); *A61N 2005/0645* (2013.01); *A61N 2005/0651* (2013.01); *A61N 2005/0664* (2013.01)

(58) Field of Classification Search
CPC ... A61N 2005/0651; A61N 2005/0664; A61M 37/00; A61M 2037/0007
See application file for complete search history.

(56) References Cited

U.S. PATENT DOCUMENTS

2019/0111278 A1* 4/2019 Tapper ................ A61N 5/0616
2020/0078212 A1   3/2020 Seo et al.

FOREIGN PATENT DOCUMENTS

| KR | 10-2012-0049085 A | 5/2012 |
| KR | 10-2013-0110365 A | 10/2013 |
| KR | 1020130110365 * | 10/2013 |
| KR | 10-2017-0138806 A | 12/2017 |
| KR | 10-2018-0038199 A | 4/2018 |
| KR | 20180092473 A | 8/2018 |
| KR | 10-1978700 B1 | 5/2019 |

* cited by examiner

LED PATCH FOR SKIN CARE APPARATUS AND SKIN CARE APPARATUS INCLUDING THE SAME

CROSS REFERENCE TO RELATED APPLICATIONS

This application is the national phase entry of International Application No. PCT/KR2020/006681, filed on May 22, 2020, designating the United States, which is based upon and claims priority to Korean Patent Application 10-2019-0063897, filed on May 30, 2019 and Korean Patent Application 10-2020-0061107, filed on May 21, 2020, the entire contents of which are incorporated herein by reference.

TECHNICAL FIELD

The present invention relates to a light-emitting diode (LED) patch for a skin care apparatus and a skin care apparatus including the same.

BACKGROUND

Recently, as a skin care method, a method has been proposed in which light in a specific wavelength band is irradiated onto skin to promote cell activity without thermal damage to tissues.

As part of this, research and development on skin care apparatuses including light sources is being actively conducted.

However, since skin care is performed in a state in which a user grips the conventional skin care apparatus with a hand, there is inconvenience in using the conventional skin care apparatus.

SUMMARY OF THE INVENTION

The present invention is directed to providing a light-emitting diode (LED) patch for a skin care apparatus which is capable of managing skin by being easily attached to user's skin, and a skin care apparatus including the same.

The present invention is also directed to providing an LED patch for a skin care apparatus which is capable of maintaining a state of being pressed against skin during use, thereby allowing a user to feel comfortable during usage and also allowing an LED to smoothly operate, and a skin care apparatus including the same.

The present invention is also directed to providing an LED patch for a skin care apparatus which is capable of providing heat to user's skin as well as light for improving the user's skin, and a skin care apparatus including the same.

One aspect of the present invention provides a light-emitting diode (LED) path for a skin care apparatus including a substrate part, a circuit pattern part formed in at least two layers on the substrate part, a light source part including one or more LEDs mounted on one surface of the substrate part, and a cover part covering at least one surface of the substrate part.

The circuit pattern part may include a first pattern formed directly on the substrate part, and a second pattern attached to one surface of the first pattern. As an example, the first pattern may be a printed pattern formed by filling pores formed in the substrate part with a conductive material, and the second pattern may be a conductive microfiber web in which a microfiber web is plated with a conductive material. In this case, the second pattern may be attached to one surface of the first pattern through a conductive adhesive layer including a vertical conductive filler.

An average pore size of the microfiber web forming the second pattern may be relatively greater than that of the substrate part.

The circuit pattern part may include a plurality of patterns which are not electrically connected to each other, and the plurality of patterns may be electrically connected to each other through the LEDs mounted on the substrate part. In this case, the plurality of patterns electrically connected to each other though the LEDs may be linear patterns or planar patterns having a predetermined area.

The LED may radiate light in a wavelength band of 405 nm to 970 nm.

The cover part may be made of a material having a moisture proof property and flexibility. As an example, the cover part may be made of a silicone material.

The cover part may include a first cover member and a second cover member which are disposed on both surfaces of the substrate part, and among the first cover member and the second cover member, the first cover member covering the LED may be a light-transmitting member, and the remaining second cover member may be a translucent member or an opaque member. Here, the first cover member may include a light diffusion material.

The LED patch may further include a support sheet having a plate shape which is disposed on a surface opposite to the one surface of the substrate part, on which the LED is mounted, and supports the substrate part. In this case, the support sheet may be made of a material having the same hardness as the substrate part or may be made of a material having hardness that is relatively greater than that of the substrate part.

The LED patch may further include a heat dissipation sheet disposed on the one surface of the support sheet.

The LED patch may further include a protective layer formed on an exposed surface of the cover part.

The LED patch may further include a heat generation part configured to generate heat when power is applied.

The heat generation part may include a base substrate having a plate shape, a lead electrode part formed along an edge of one surface of the base substrate and including lead electrodes which are not physically connected to each other, a branch electrode part including branch electrodes which are not electrically connected to each other and which each extend from the lead electrode such that partial lengths thereof face each other, and a conductive heat generation material which has a predetermined area, is formed to be located at overlapping portions of the branch electrodes facing each other, and generates heat while electrically conducting the branch electrodes when power is supplied.

The light source part may include the plurality of LEDs mounted on the one surface of the substrate part, the heat generation part may include the plurality of branch electrode parts spaced apart from each other by a predetermined interval along a length direction of the lead electrode, and the plurality of conductive heat generation materials provided at each of the plurality of branch electrode parts, and the plurality of branch electrode parts and the plurality of conductive heat generation materials may be disposed to be located at positions that do not overlap the plurality of LEDs.

The base substrate may include a film member having an insulating property, and a porous substrate stacked on one surface of the film member, and the lead electrode part and the branch electrode part may be formed on the porous substrate.

The LED patch may further include a connection cable configured to supply power supplied from the outside toward the light source part.

The connection cable may be electrically connected to the light source part through a circuit board disposed such that a partial area thereof overlaps the substrate part.

The connection cable may include a connected port to be connected provided at one end thereof so as to be connected to an external power supply device, and the external power supply device may be a portable electronic device or an auxiliary battery.

Another aspect of the present invention a skin care apparatus including the above-described at least one LED patch for a skin care apparatus, a connection part configured to electrically connect an external power supply device and a connection cable of the LED patch for a skin care apparatus to each other, and a control part provided in the connection part to control overall driving of the light source part.

The external power supply device may be a portable electronic device or an auxiliary battery.

The LED patch may include an embedded battery, and the light source part may receive driving power from the battery.

According to the present invention, elasticity and flexibility can be secured so that a light-emitting diode (LED) path can be easily attached even to a curved adherend region, and adhesion to skin can be increased so that a user can feel comfortable during usage. Accordingly, according to the present invention, in a state in which the user attaches the LED patch to skin, the skin can be managed, thereby increasing usage convenience.

In addition, according to the present invention, the LED patch has elasticity and flexibility, and also, conduction stability between the LED and a circuit pattern part is secured, thereby increasing reliability.

Furthermore, according to the present invention, heat as well as light for improving user's skin are provided to the user's skin, thereby promoting the skin penetration of active ingredients applied on the user's skin.

DETAILED DESCRIPTION OF THE INVENTION

Figure 1:
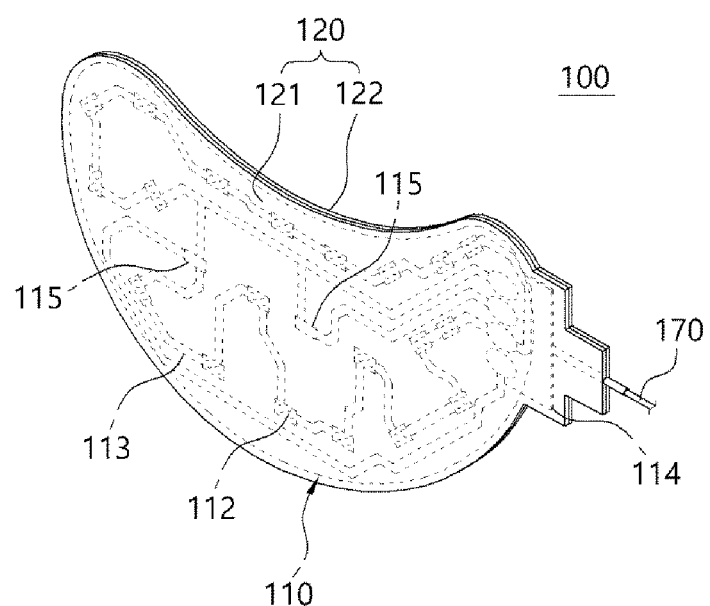
FIG. 1 is a view illustrating a light-emitting diode (LED) patch for a skin care apparatus according to one embodiment of the present invention.

Hereinafter, embodiments of the present invention will be described in detail with reference to the accompanying drawings so as to be easily practiced by a person of ordinary skill in the art to which the present invention pertains. It should be understood that the present invention may be embodied in various different forms and is not limited to the following embodiments. Parts irrelevant to description are omitted in the drawings in order to clearly describe the present invention, and like reference numerals refer to like elements throughout the specification.

A light-emitting diode (LED) patch 100, 100', or 200 for a skin care apparatus according to one embodiment of the present invention may radiate light in a predetermined wavelength band toward user's skin through a light source in a state of being attached to the user's skin.

Accordingly, a user can obtain beneficial effects using light irradiated from the LED patch 100, 100', or 200 for a skin care apparatus according to one embodiment of the present invention.

For example, the beneficial effects may include a skin soothing effect, skin texture improvement, sensitive skin soothing care, skin contour improvement, skin elasticity improvement, skin elasticity restoration, skin lifting improvement, skin gloss improvement, and the like.

In this case, the LED patch 100, 100', or 200 for a skin care apparatus according to one embodiment of the present invention may be attached to the user's skin even without using a separate adhesive or adhesive agent and may maintain a state of being pressed against a curved adherend region such as a face.

As an example, the LED patch 100, 100', or 200 for a skin care apparatus according to one embodiment of the present invention may be attached to the user's skin through a material in a liquid or gel phase such as an ampoule material, an essence material, or cosmetics applied on the user's skin.

In addition, in the LED patch 100, 100', or 200 for a skin care apparatus according to one embodiment of the present invention, one surface thereof facing the user's skin may be attached directly to the user's skin even without using a separate member or material.

To this end, as shown in FIGS. 1, 2, 5, 6, 9, and 10, the LED patch 100, 100', or 200 for a skin care apparatus according to one embodiment of the present invention may include a light source part 110 or 110' and a cover part 120.

Figure 3:
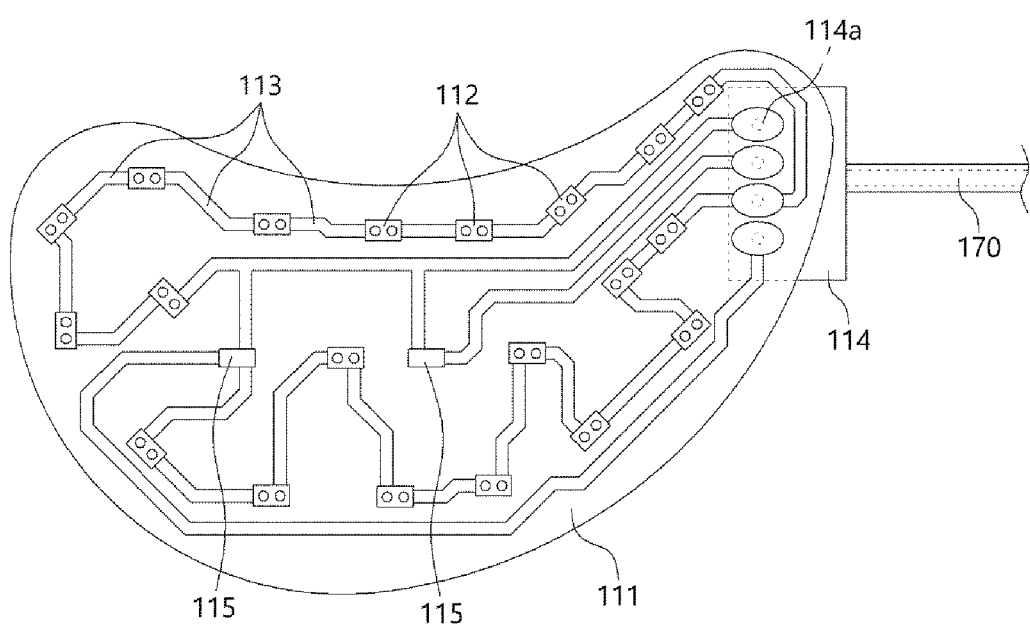
FIG. 3 is a plan view illustrating a state in which a cover part is removed in FIG. 1.
Figure 7:
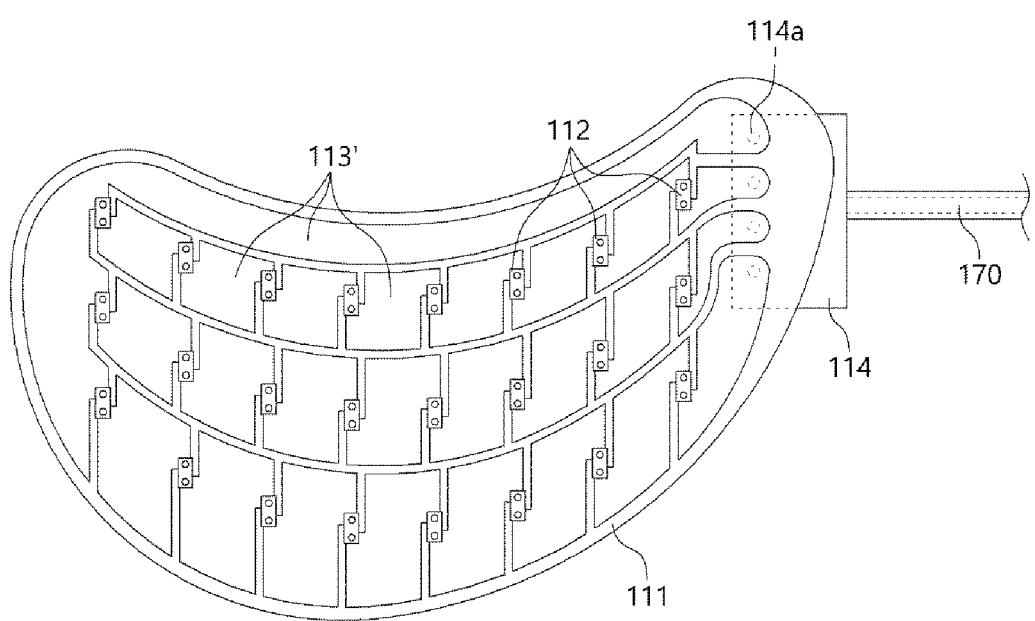
FIG. 7 is a plan view illustrating a state in which a cover part is removed in FIG. 5.
Figure 11:
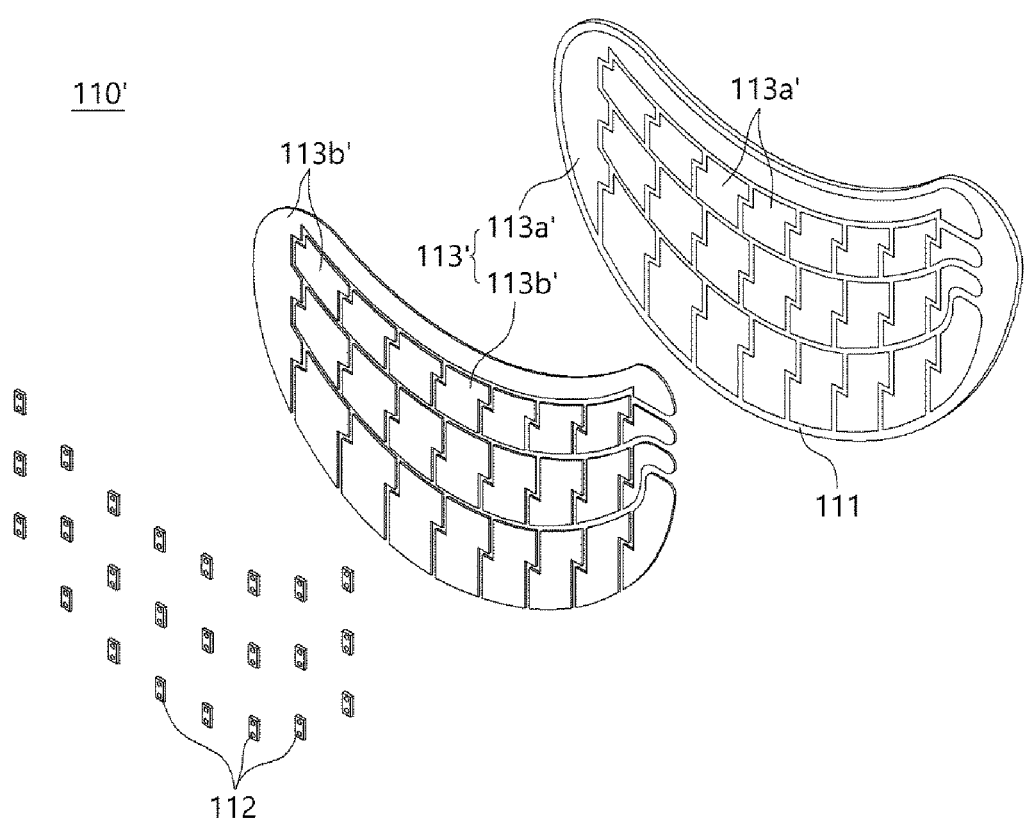
FIG. 11 is an exploded view illustrating a detailed configuration of a light source part in FIG. 10.

The light source part 110 or 110' may generate light in a predetermined wavelength band when power is supplied. To this end, as shown in FIGS. 3, 7, and 11, the light source part 110 or 110' may include a substrate part 111, a circuit pattern part 113 or 113' formed on the substrate part 111, and one or more LEDs 112 mounted on one surface of the substrate part 111 through the circuit pattern part 113 or 113'.

In this case, the substrate part 111 may be a plate-shaped member having a predetermined area, the LED 112 may be provided as a plurality of LEDs 112, and the plurality of LEDs 112 may be mounted on one surface of the substrate part 111 through the circuit pattern part 113 or 113'.

Thus, the plurality of LEDs 112 may be arranged in a predetermined pattern on one surface of the substrate part 111 and may be electrically connected to each other through the circuit pattern part 113 or 113'.

Accordingly, the light source part 110 or 110' may form a surface light source through the plurality of LEDs 112 arranged on one surface of the substrate part 111, and the LED patch 100, 100', 200 for a skin care apparatus according to one embodiment of the present invention can radiate light to the user's skin over a wide area using light generated in the form of surface light source from the light source part 110 or 110'.

In this case, the substrate part 111 may have flexibility and elasticity. Accordingly, even when the LED patch 100, 100', or 200 for a skin care apparatus according to one embodiment of the present invention is attached to a curved body region such as a face, the LED patch 100, 100', or 200 for a skin care apparatus may be transformed in response to the curved body region to maintain the form of a surface light source.

To this end, the substrate part 111 may be formed as a porous substrate having pores.

As an example, the porous substrate may be cloth, a fabric, a nonwoven fabric, a porous film, a membrane, and the like. However, the porous substrate is not limited to the above-described materials, and any material may be used without limitation as long as the material has pores with a predetermined size while having elasticity and flexibility.

Figure 14:
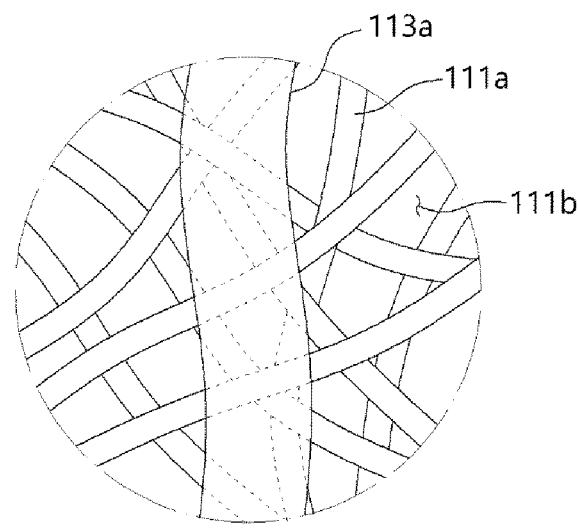
FIG. 14 is a schematic view illustrating a first pattern applicable to an LED patch for a skin care apparatus according to the present invention.

As a specific example, as shown in FIG. 14, the substrate part 111 may be a nanofiber web in which nanofibers 111a including a synthetic polymer are accumulated in a three-dimensional network structure so as to have pores 111b.

In this case, the circuit pattern part 113 or 113' may be formed on at least one surface of the substrate part 111. Accordingly, the substrate part 111 may serve as a circuit board on which electronic components such as the LEDs 112 may be mounted.

Accordingly, in the LED patch 100, 100', or 200 for a skin care apparatus according to one embodiment of the present invention, when the substrate part 111 is formed of the nanofiber web, the substrate part 111 may have superior bending properties compared to a polyimide film used as a typical flexible circuit board and may have excellent restoration properties capable of being returned to its original state even when folded or crumpled.

As a non-limiting example, the substrate part 111 may be a single-layered or multi-layered nanofiber web in which a spinning solution prepared by mixing a synthetic polymer and a solvent is electrospun and accumulated to have the pores 111b. Here, the solvent may be water or alcohol, and in addition to water or alcohol, an organic solvent such as dimethylacetamide or acetone may be used alone or may be mixed with each other.

In this case, the synthetic polymer may be a fiber-forming polymer capable of implementing a nanofiber web through electrospinning while having flexibility and elasticity. As a specific example, polyvinylidene fluoride (PVDF) may be used alone as the synthetic polymer, but PVDF and polyethersulfone (PES) may be used by being mixed in a predetermined ratio so as to secure heat resistance against a high temperature when the LED 112 is soldered.

However, the material of the synthetic polymer is not limited thereto, and any fiber-forming polymer may be used without limitation as long as the fiber-forming polymer has flexibility and elasticity while being capable of implementing a nanofiber web through electrospinning.

As described above, in the LED patches 100, 100', or 200 for a skin care apparatus according to one embodiment of the present invention, since the substrate part 111 is formed as a porous substrate having flexibility and elasticity, the LED patches 100, 100', or 200 for a skin care apparatus according to one embodiment of the present invention can secure flexibility and elasticity. Accordingly, even when attached to a curved body region such as a face, the LED patch 100, 100', or 200 for a skin care apparatus according to one embodiment of the present invention may be transformed in response to the curved body region, thereby increasing adhesion with the skin.

In addition, in the LED patch 100, 100' or, 200 for a skin care apparatus according to one embodiment of the present invention, since the substrate part 111 for mounting the LED 112 may be formed of a nanofiber web to have a very thin thickness, the LED patch 100, 100', or 200 for a skin care apparatus according to one embodiment of the present invention can be implemented in a slim form.

Accordingly, even when the LED patch 100, 100', 200 for a skin care apparatus according to one embodiment of the present invention is attached to the user's skin through a material such as cosmetics or an ampoule material, the possibility that the LED patch 100, 100', and 200 for a skin care apparatus according to one embodiment of the present invention is separated from the user's skin can be significantly reduced.

The circuit pattern part 113 or 113' may be formed in a predetermined pattern on at least one surface of the substrate part 111 and may electrically connect the electronic components mounted on the substrate part 111 to each other.

As an example, the circuit pattern part 113 or 113' may include a plurality of patterns that are not electrically connected to each other. Here, the plurality of patterns that are not electrically connected to each other may be electrically connected to each other through the electronic components such as the LEDs 112 or temperature sensors 115 mounted on one surface of the substrate part 111.

In addition, the plurality of patterns may be formed in a linear shape as shown in FIGS. 1 to 4 or may be formed in a planar shape having a predetermined area as shown in FIGS. 5 to 11.

In this case, the circuit pattern part 113 or 113' may be formed to maintain conduction stability even when the substrate part 111 is made of a material having elasticity and flexibility.

That is, the circuit pattern part 113 or 113' may include at least two layers stacked on each other to maintain conduction stability even when the substrate part 111 is stretched and contracted.

Figure 4:
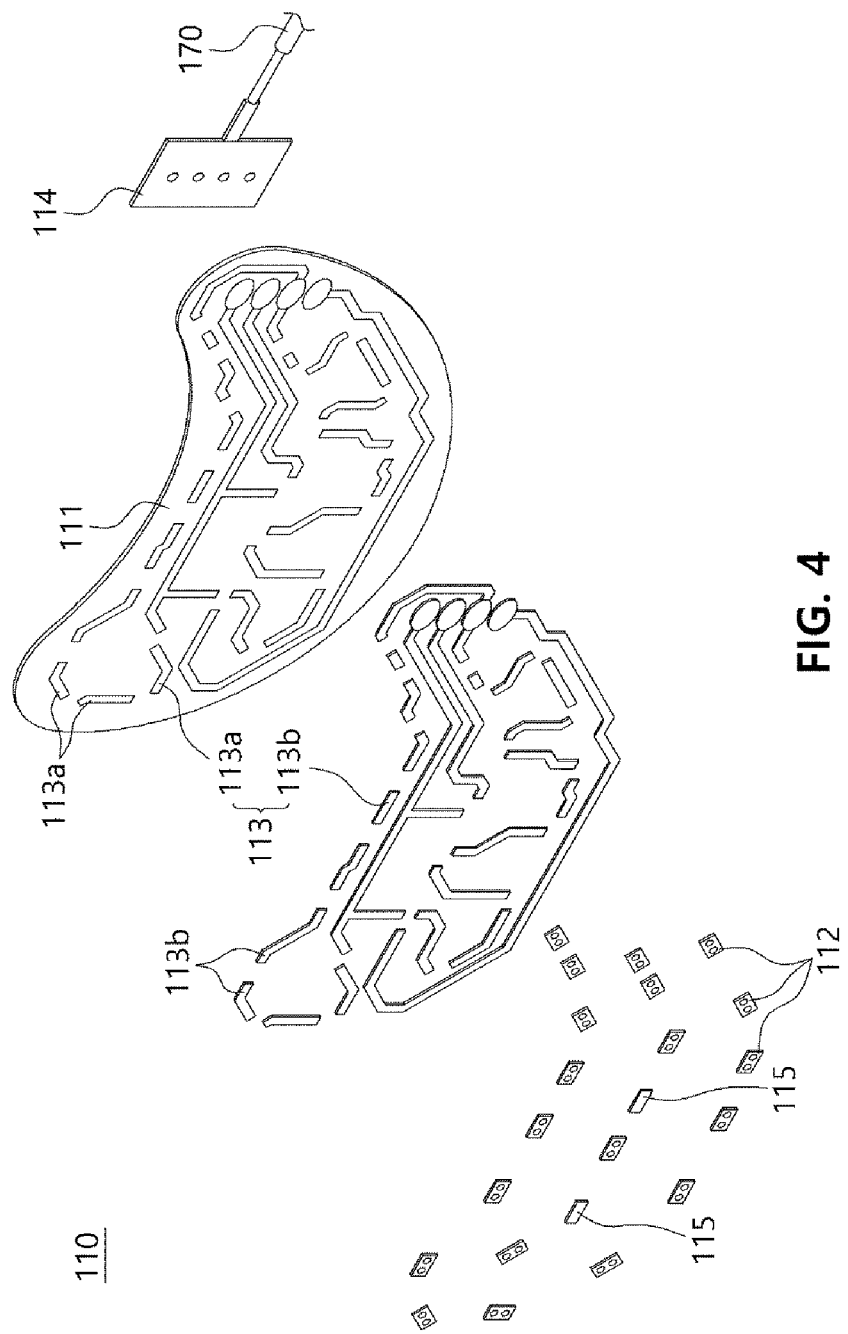
FIG. 4 is an exploded view illustrating a detailed configuration of a light source part applicable to FIG. 3.
Figure 8:
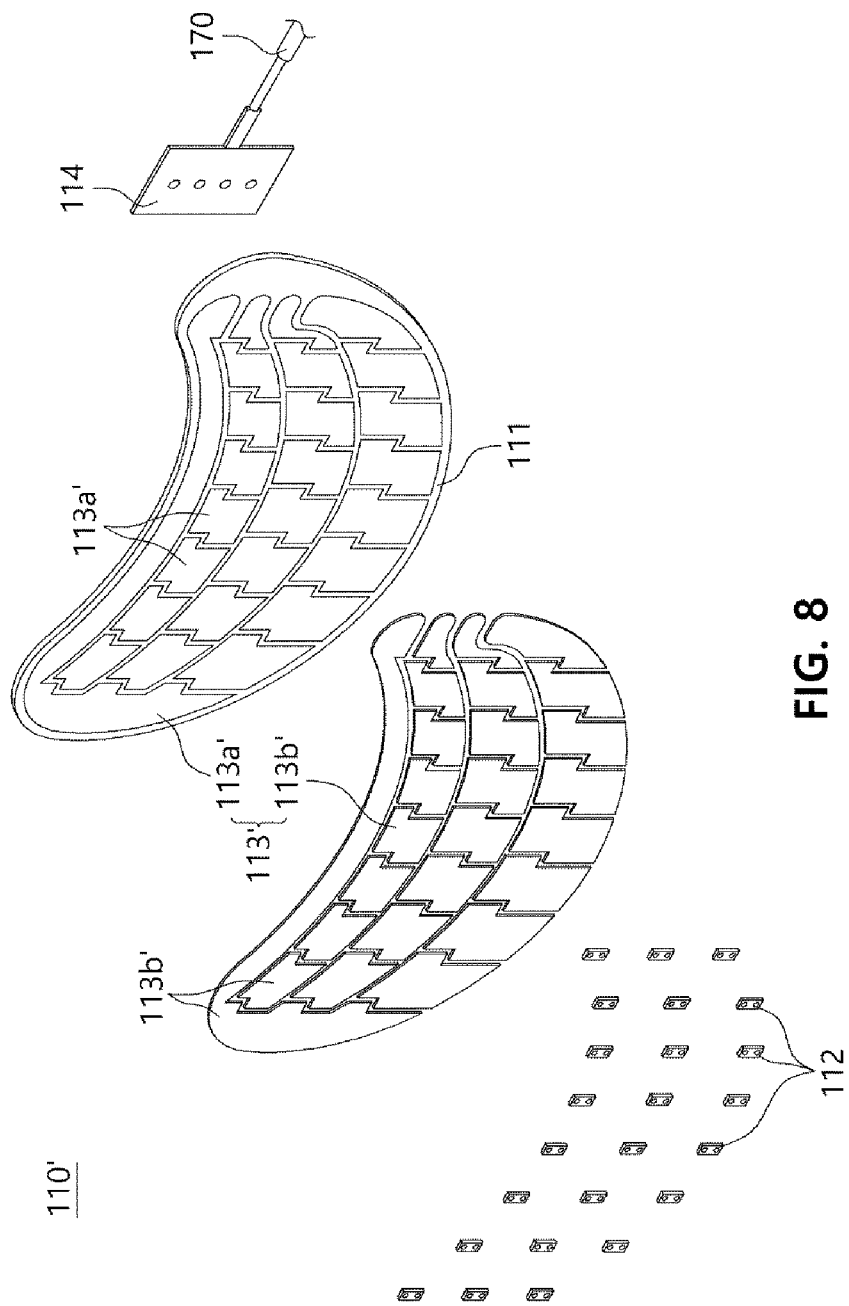
FIG. 8 is an exploded view illustrating a detailed configuration of a light source part applicable to FIG. 7.

As an example, as shown in FIGS. 4, 8, and 11, the circuit pattern part 113 or 113' may include a first pattern 113a or 113a' formed directly on the substrate part 111 and a second pattern 113b or 113b' attached to one surface of the first pattern 113a or 113a', and the LED 112 may be mounted on one surface of the second pattern 113b or 113b'.

Specifically, the first pattern 113a or 113a' may be a printed pattern formed directly on the substrate part 111 such that a conductive material fills the pores 111b of the substrate part 111 as shown in FIG. 14.

That is, the first pattern 113a or 113a' may be a printed pattern formed directly on the substrate part 111 through a printing method using a conductive paste, and the conductive paste may completely or partially fill the pores 111b formed in the substrate part 111 along with a surface of the substrate part 111. Here, the conductive paste may be a silver (Ag) paste but is not limited thereto, and any known conductive paste may be applied.

Figure 15:
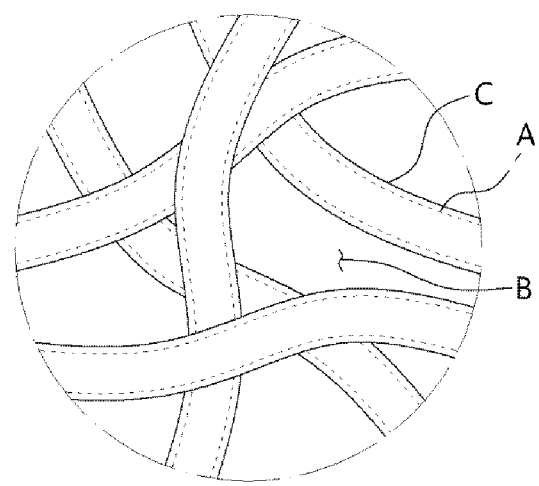
FIG. 15 is a schematic view illustrating a second pattern applicable to an LED patch for a skin care apparatus according to the present invention.

In addition, the second pattern 113b or 113b' may be a conductive microfiber web in which a microfiber web, in which microfibers A are formed to have pores B, is plated with a conductive material C. That is, the second pattern 113b or 113b' may be formed of the conductive microfiber web in which the conductive material C is applied to surround surfaces of the microfibers A constituting the microfiber web as shown in FIG. 15.

Accordingly, the second pattern 113b or 113b' may have elasticity and flexibility like the substrate part 111, and when the substrate part 111 is stretched or contracted by an external force, the second pattern 113b or 113b' may be stretched or contracted like the substrate part 111.

In this case, the second pattern 113b or 113b' may be formed by punching the conductive microfiber web, in which the conductive material is applied to surround the surfaces of the microfibers A constituting the microfiber web, so as to have the same pattern shape as the first pattern 113a or 113a' formed directly on the substrate part 111.

Such a second pattern 113b or 113b' may be attached to one surface of the first pattern 113a or 113a' through a conductive adhesive layer. Here, the conductive adhesive layer may be an adhesive layer including a vertical conductive filler such as nickel (Ni).

Accordingly, the first pattern 113a or 113a' and the second pattern 113b or 113b' may have the same pattern shape, and the first pattern 113a or 113a' and the second pattern 113b or 113b' may be electrically connected to each other through the conductive adhesive layer.

As described above, in the LED patch 100, 100', or 200 for a skin care apparatus according to one embodiment of the present invention, the first pattern 113a or 113a' and the second pattern 113b or 113b' formed in different manners are stacked to constitute the circuit pattern part 113 or 113', thereby increasing the conduction stability of the circuit pattern part 113 or 113'.

That is, when the substrate part 11 having elasticity and flexibility is stretched or contracted in a use process, the first pattern 113a or 113a' and the second pattern 113b or 113b' formed in different manners may mutually complement a short circuit so that the LED 112 may be stably operated.

When the circuit pattern part 113 or 113' includes only the first pattern 113a or 113a' formed directly on the substrate part 111 and the LED 112 is mounted on the first pattern 113a or 113a', and when the substrate part 111 is bent or crumpled by an external force, cracks may occur in the first patterns 113a or 113'. Accordingly, the LED 112 mounted on the first pattern 113a or 113a' may not stably receive power due to the cracks occurring in the first patterns 113a or 113a'.

On the other hand, when the circuit pattern part 113 or 113' includes only the second pattern 113b or 113b' formed of the conductive microfiber web and the LED 112 is mounted on the second pattern 113b or 113b', and when the substrate part 111 is stretched or contracted by an external force, a cross-sectional area of the second pattern 113b or 113b' may be decreased or increased. Accordingly, a resistance applied to the circuit pattern part may be varied by a change in cross-sectional area of the second pattern 113b or 113b'. For this reason, since a resistance applied to the LEDs 112 is also varied, the LEDs 112 may not emit light uniformly.

In the present invention, since the first pattern 113a or 113a' and the second pattern 113b or 113b' formed in different manners are stacked on each other to constitute the circuit pattern part 113 or 113', the possibility of an electrical short circuit through the second pattern 113b or 113b' may be reduced and also a change in resistance through the first pattern 113a or 113a' may be cancelled out.

Accordingly, in the LED patch 100, 100', and 200 for a skin care apparatus according to one embodiment of the present invention, it is possible to maintain the conduction stability of the circuit pattern part 113 or 113'.

For this reason, in the LED patch 100, 100', 200 for a skin care apparatus according to one embodiment of the present invention, since the LED 112 mounted on the second pattern 113b or 113b' can be stably operated, reliability can be increased.

In addition, in the LED patch 100' or 200 for a skin care apparatus according to one embodiment of the present invention, when the first pattern 113a' and the second pattern 113b', which are formed in a planar shape having a predetermined area as shown in FIGS. 5 to 11, are stacked to form the circuit pattern part 113', a contact area between the first pattern 113a' and the second pattern 113b' may be increased. Accordingly, in the LED patch 100' or 200 for a skin care apparatus according to the present embodiment, it is possible to further increase conduction stability.

However, in the LED patch 100, 100', or 200 for a skin care apparatus according to one embodiment of the present invention, the configuration of the circuit pattern part 113 or 113' is not limited thereto, and the circuit pattern part 113 or 113' may include only the first pattern 113a or 113a' or only the second pattern 113b or 113b'.

Meanwhile, in the LED patch 100, 100', or 200 for a skin care apparatus according to one embodiment of the present invention, an average pore size of the microfiber web constituting the second pattern 113b or 113b' may be relatively greater than that of a porous substrate which is the substrate part 111.

Accordingly, when the LEDs 112 are mounted on the second pattern 113b or 113b', a solder paste for mounting the LEDs 112 may sufficiently penetrate into the pores B of the conductive microfiber web constituting the second pattern 113b or 113b' but may not penetrate into the pores 111b of the substrate part 111 on which the first pattern 113a or 113a' is formed.

For this reason, the LEDs 112 mounted on the second pattern 113b or 113b' may form a strong bond with the second pattern 113b or 113b' through the solder paste.

As an example, the average pore size of the microfiber web constituting the second pattern 113b or 113b' may be in a range of 5 μm to 15 μm, and the average pore size of the substrate part 111 may be in a range of 0.1 μm to 2 μm. However, the average pore size is not limited thereto and may be appropriately changed according to design conditions as long as the average pore size of the microfiber web constituting the second pattern 113b or 113b' is relatively greater than that of the substrate part 111.

The LED 112 may generate light having a predetermined wavelength band when power is supplied.

One or more LEDs 112 may be provided, and preferably, the plurality of LEDs 112 may be provided to form a surface light source. In addition, the plurality of LEDs 112 may be spaced a certain interval apart from each other.

Accordingly, in the LED patch 100, 100', or 200 for a skin care apparatus according to one embodiment of the present invention, the plurality of LEDs 112 are disposed in a dispersed form on one surface of the substrate part 111 having a plate shape, thereby implementing a surface light source. For this reason, the LED patch 100, 100', or 200 for a skin care apparatus according to one embodiment of the present invention can radiate light onto the user's skin over a wide area.

In this case, the LEDs 112 may emit light in one wavelength band. For example, the LEDs 112 may emit light in a band of 405 nm to 420 nm which can be absorbed by skin epithelial tissues, thereby destroying bacteria and treating acne.

However, a wavelength band of the LEDs 112 is not limited thereto, and the LED 112 may radiate light in any wavelength band suitable for a desired skin improvement effect among bands of 405 nm to 970 nm.

In addition, the LEDs 112 may radiate light in one wavelength band and may be provided to radiate pieces of light in different wavelength bands. As a non-limiting example, as the LEDs 112, a plurality of light-emitting elements may be integrally formed to emit pieces of light in different wavelength bands. Alternatively, the LED 112 may be provided as a plurality of LEDs, and the plurality of LEDs may include two or more LEDs radiating pieces of light in different wavelength bands.

Meanwhile, the light source part 110 may further include one or more temperature sensors 115 mounted on one surface of the substrate part 111. Such a temperature sensor 115 may measure a temperature generated when the LED 112 emits light.

Here, an appropriate number of the temperature sensors 115 may be mounted on one surface of the substrate part 111 and may be dispersed and disposed to measure a temperature at various positions.

The cover part 120 may cover at least one surface of the substrate part 111. As an example, the cover part 120 may be provided on at least one surface of the substrate part 111 so as to surround the light source part 110 or 110'.

Accordingly, the cover part 120 can prevent external exposure of the light source part 110 or 110' and can block liquid phase materials, such as moisture applied on the user's skin, from moving toward the light source part 110 or 110'.

To this end, the cover part 120 may be a plate-shaped sheet having a predetermined area so as to cover the light source part 110 or 110'.

Such a cover part 120 may be made of a polymer resin such as polyurethane (PU), polyethylene terephthalate (PET), polypropylene (PP), polyethylene (PE), or polyvinylidene fluoride (PVDF), or a material such as release paper, a fabric, or a leather and may also be formed as a molded body covered by a resin material including an insulant.

In addition, the cover part 120 may be made of a silicone material.

Here, when the cover part 120 is made of a silicone material, the cover part forming a contact surface in contact with the user's skin may have a hardness of 5 to 20.

Typically, silicone with a hardness of 5 to 20 may have a very sticky surface. In the present invention, since the cover part forming the contact surface in contact with the user's skin is made of a silicone material having a hardness of 5 to 20, the cover part may be attached directly to the user's skin even without using a material in a liquid or gel phase such as a separate adhesive, adhesive agent, ampoule material, essence material, or cosmetics.

Meanwhile, the cover part 120 may be made of a material having flexibility and pliability. In addition, the cover part 120 may be made of a material having a moisture proof property as well as flexibility and pliability so as to block movement of moisture.

Figure 5:
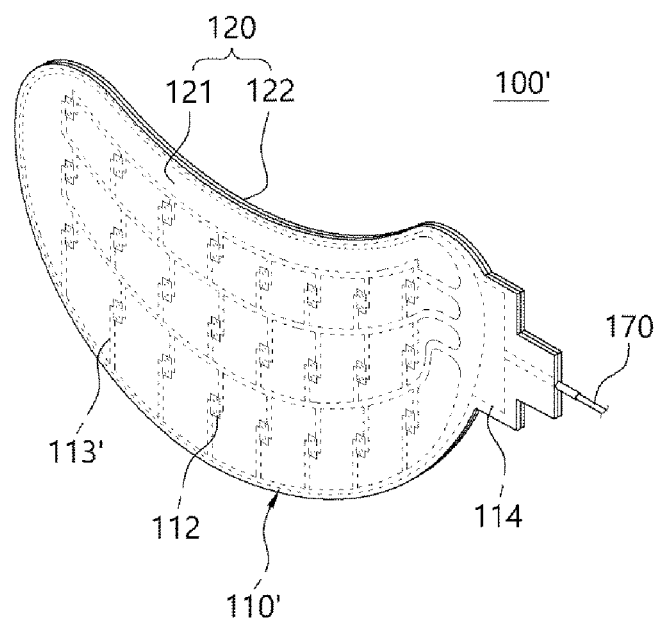
FIG. 5 is a view illustrating an LED patch for a skin care apparatus according to another embodiment of the present invention.
Figure 9:
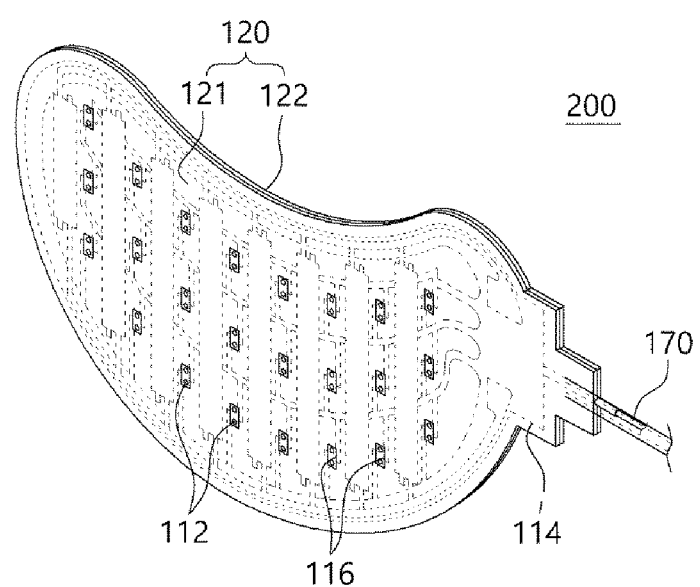
FIG. 9 is a view illustrating an LED patch for a skin care apparatus according to still another embodiment of the present invention.

As a specific example, the cover part 120 may include one pair of cover members 121 and 122 as shown in FIGS. 1, 5, and 9, and the one pair of cover members 121 and 122 may include a first cover member 121 and a second cover member 122 which are disposed on both surfaces of the substrate part 111.

The first cover member 121 and the second cover member 122 may be attached to each other through an adhesive layer or fixed to each other through thermal fusion. Here, the adhesive layer may be a non-substrate type in a liquid or gel phase or a substrate type in which an adhesive material is applied to both surfaces of a substrate.

In addition, the first cover member 121 may be a cover member that covers one surface of the substrate part 111 on which the LED 112 is mounted, and the second cover member 122 may be a cover member that covers one surface of the substrate part 111 on which the LED 112 is not mounted. In this case, an outer surface of the first cover member 121 may be a contact surface in contact with the user's skin.

In this case, the LED patch 100 or 100' for a skin care apparatus according to one embodiment of the present invention may be configured to limit an irradiation direction of light generated by the LED 112. In addition, the LED patch 100 or 100' for a skin care apparatus according to one embodiment of the present invention may scatter or diffuse light generated from the LED 112 which is a point light source, thereby emitting the light generated from the LED 112 to the outside in the form of surface light source.

That is, the first cover member 121 may have a light-transmitting property to transmit light, and the second cover member 122 may have a translucent or opaque property to block the passage of light. In addition, the first cover member 121 may include a light diffusion material such as $TiO_2$.

As an example, the first cover member 121 may be made of a transparent silicone material in which a $TiO_2$ powder and silicon are mixed, and the second cover member 122 may be made of a silicone material in which a colored pigment and silicon are mixed.

Accordingly, light generated from the LED 112 may be diffused or scattered while passing through the first cover member 121, thereby being irradiated toward the user's skin in the form of surface light source and being blocked from being emitted to the outside through the second cover member 122.

Alternatively, in the LED patch 200 for a skin care apparatus according to one embodiment of the present invention, light generated from the LED 112 may be irradiated directly toward the user's skin.

Figure 10:
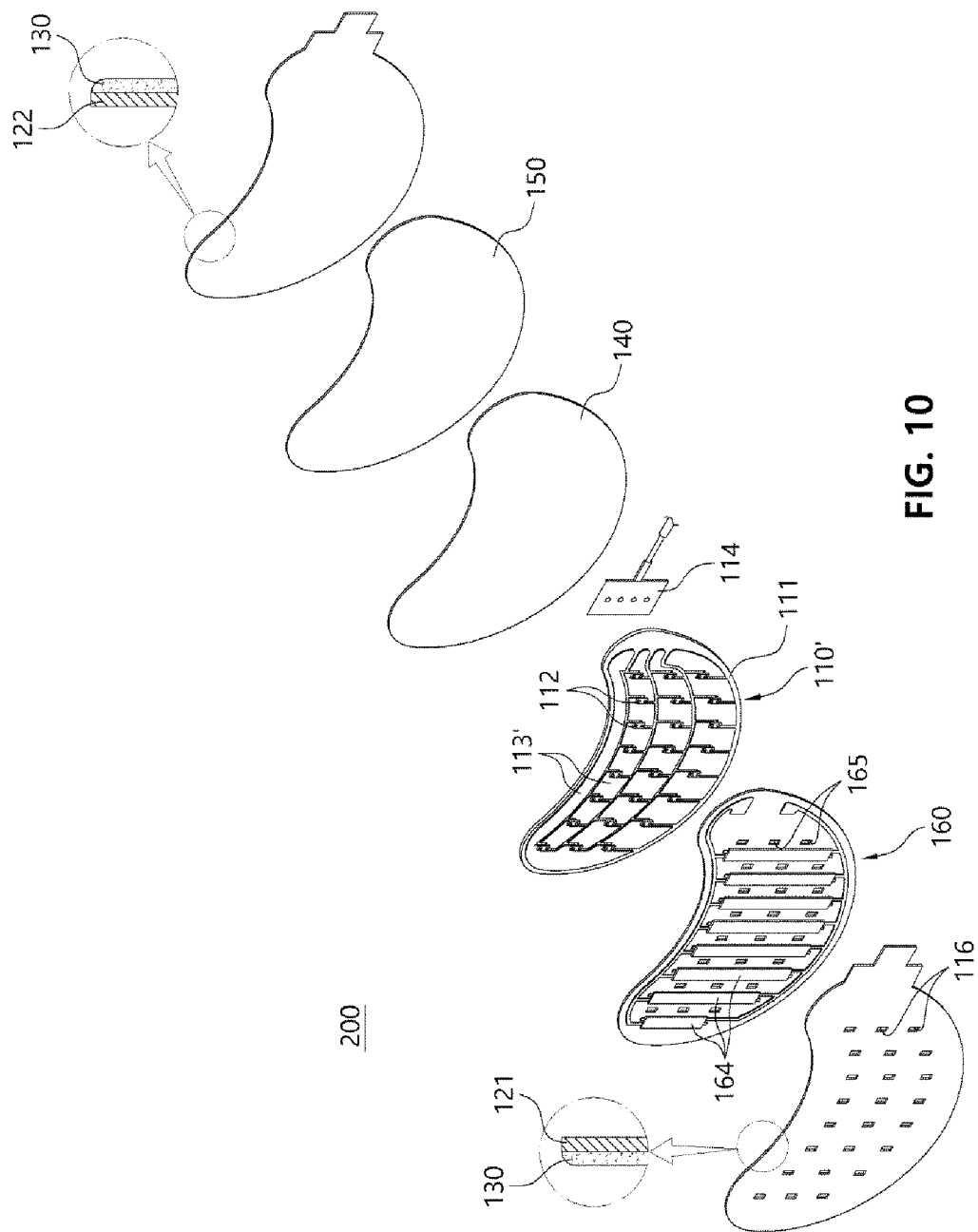
FIG. 10 is an exploded view of FIG. 9.

That is, as shown in FIGS. 9 and 10, the first cover member 121 may include arrangement holes 116 formed to pass through regions corresponding to the LEDs 112, and the LEDs 112 may be exposed to the outside through the arrangement holes 116.

Accordingly, light generated from the LED 112 may be irradiated directly toward the user's skin through the arrangement hole 116.

Figure 2:
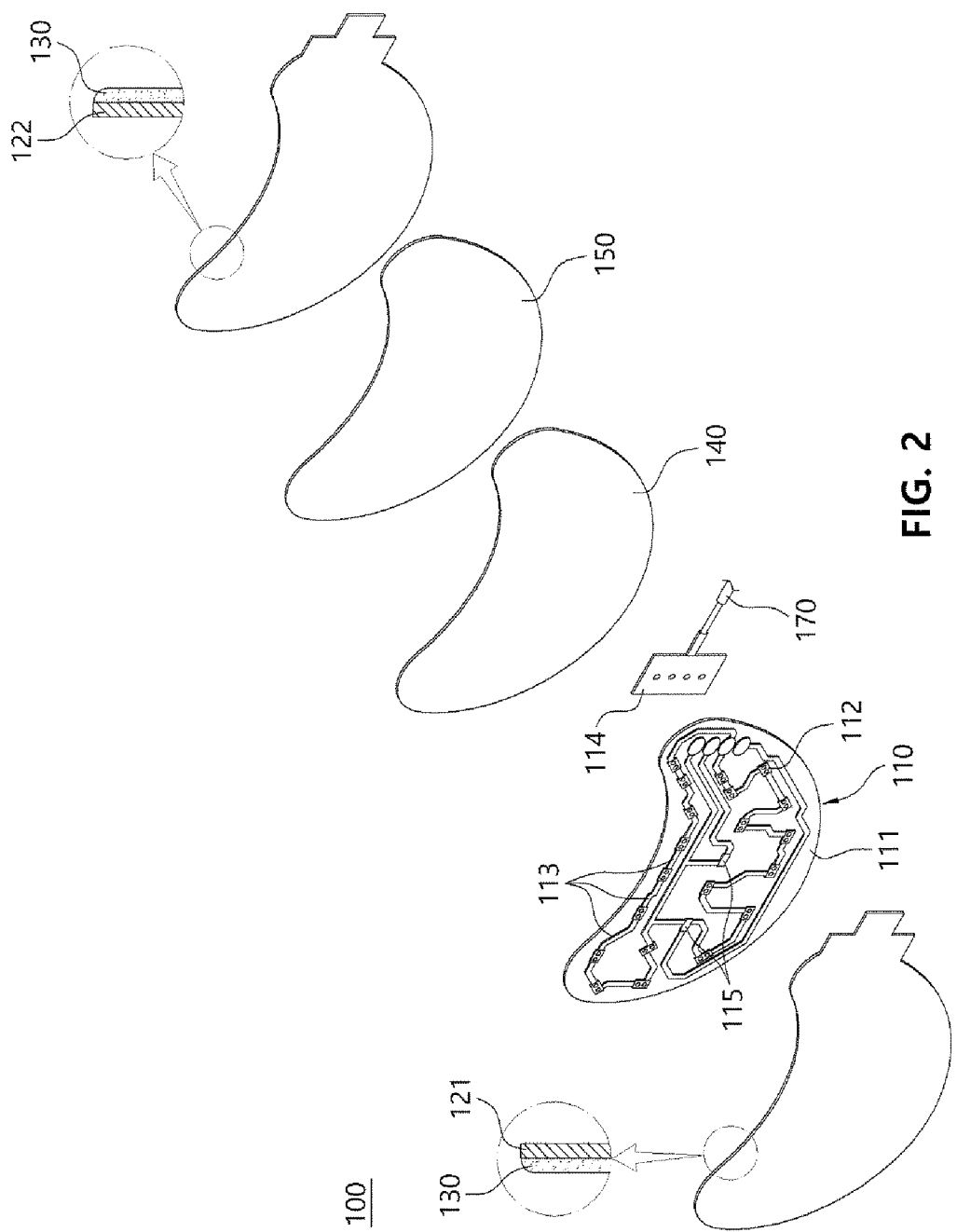
FIG. 2 is an exploded view of FIG. 1.
Figure 6:
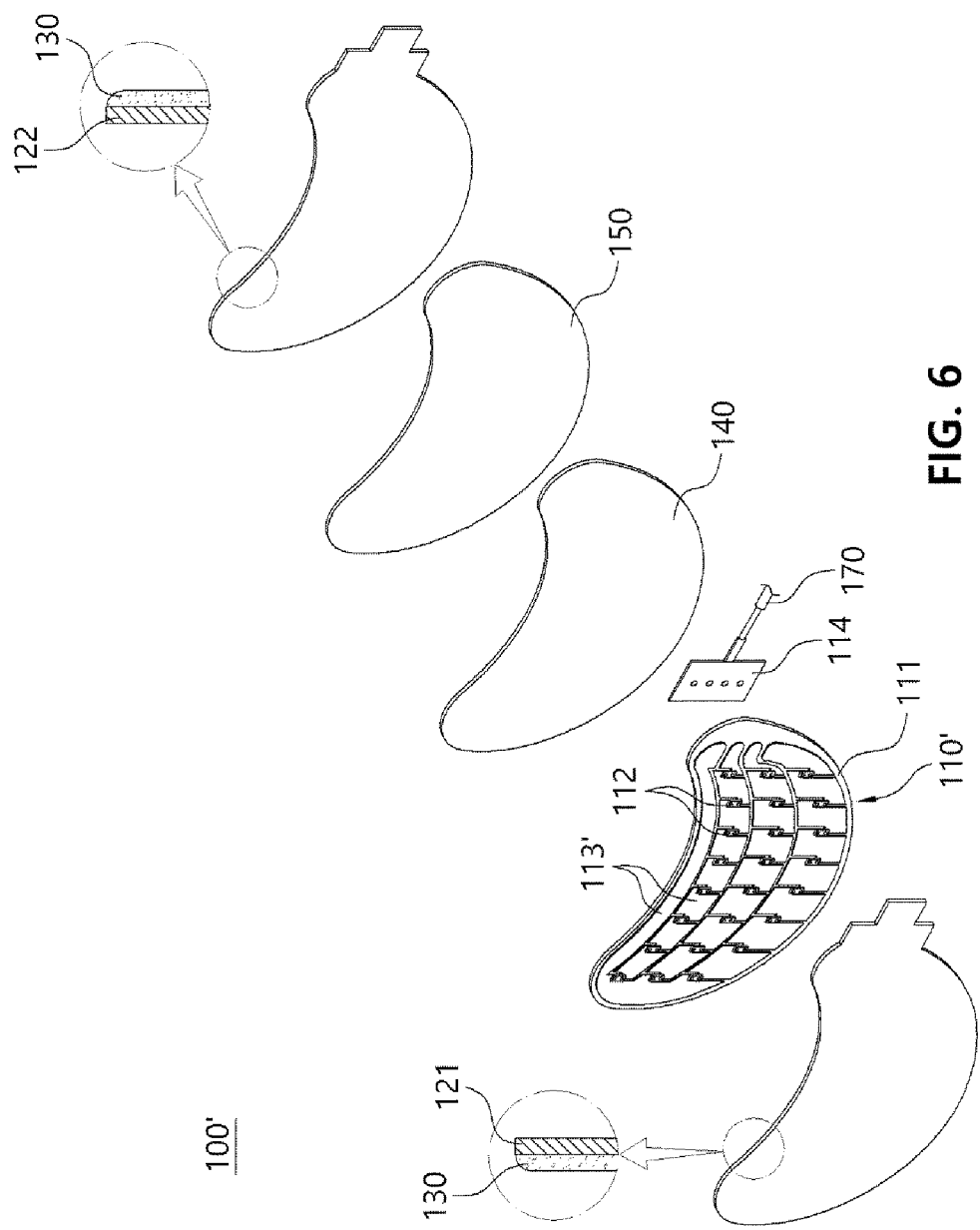
FIG. 6 is an exploded view of FIG. 5.

In the present invention, as shown in enlarged views of FIGS. 2, 6, and 10, the LED patch 100, 100', or 200 for a skin care apparatus may further include a protective layer 130 formed on an exposed surface of the cover part 120.

As an example, the protective layer 130 may be formed only on an exposed surface of the first cover member 121 in contact with the user's skin in the cover part 120 or may be formed on both of the exposed surface of the first cover member 121 and an exposed surface of the second cover member 122.

Such a protective layer 130 can prevent foreign materials such as dust from adhering to the exposed surface of the cover part 120 and can increase adhesiveness with the user's skin using a material in a liquid or gel phase such as an ampoule material, an essence material, or cosmetics applied on the user's skin.

As a non-limiting example, the protective layer 130 may be made of PU. In addition, the protective layer 130 may be formed as a coating layer applied to a predetermined thickness on one surface of the cover part 120 or may be a thin film member attached on the one surface of the cover part 120.

Meanwhile, the LED patch 100, 100', or 200 for a skin care apparatus according to one embodiment of the present invention may further include a support sheet 140 disposed between the cover part 120 and the substrate part 111.

Referring to FIGS. 2, 6, and 10, the support sheet 140 may be a sheet having a plate shape and may be disposed on a surface opposite to a surface of the substrate part 111 on which the LED 112 is mounted.

As an example, the support sheet 140 may be disposed between the substrate part 111 and the second cover member 122 and may support one surface of the substrate part 111.

In this case, the support sheet 140 may have hardness that is relatively greater than that of the substrate part 111 while having flexibility.

As a specific example, the support sheet 140 may be a thin film member, and the thin film member may be laminated on one surface of the substrate part 111.

As a non-limiting example, the support sheet 140 may be a PU film, but the material of the support sheet 140 is not limited thereto. Any material may be used without limitation as long as the material has hardness that is relatively greater than that of the substrate part 111 while having flexibility.

Accordingly, even when the substrate part 111 is formed of a membrane, the support sheet 140 may support one surface of the substrate part 111 to maintain the substrate part 111 in an unfolded state. That is, the support sheet 140 may serve to maintain the substrate part 111 in a plate shape while complementing the strength of the substrate part 111. Accordingly, the user can easily handle the substrate part 111.

Meanwhile, the LED patch 100, 100', or 200 for a skin care apparatus according to one embodiment of the present invention may further include a heat dissipation sheet 150.

As shown in FIGS. 2, 6, and 10, such a heat dissipation sheet 150 may be disposed between the support sheet 140 and the second cover member 122.

In this case, the heat dissipation sheet 150 may be made of a material having excellent thermal conductivity. As an example, the heat dissipation sheet 150 may be made of a metal material such as copper or aluminum, but the present invention is not limited thereto. The heat dissipation sheet 150 may be made of graphite, or any known material used as a heat dissipation member may be applied.

Such a heat dissipation sheet 150 may absorb heat generated in a reflow process for mounting the LED 112 on the circuit pattern part 113 or 113' or may absorb heat generated from the LED 112 in a usage process.

Accordingly, the LED patch 100, 100', or 200 for a skin care apparatus according to one embodiment of the present invention may absorb heat through the heat dissipation sheet 150 so that thermal damage due to a high temperature can be prevented in advance.

Meanwhile, the LED patch 200 for a skin care apparatus according to one embodiment of the present invention may further include a heat generation part 160.

As an example, as shown in FIGS. 9 and 10, the heat generation part 160 may be disposed between the light source part 110' and the first cover member 121.

The heat generation part 160 may generate and provide heat toward the user's skin, thereby promoting the skin penetration of active ingredients applied on the user's skin.

In this case, the heat generation part 160 may be implemented to generate heat at a constant temperature regardless of a position of a heating part.

Figure 12:
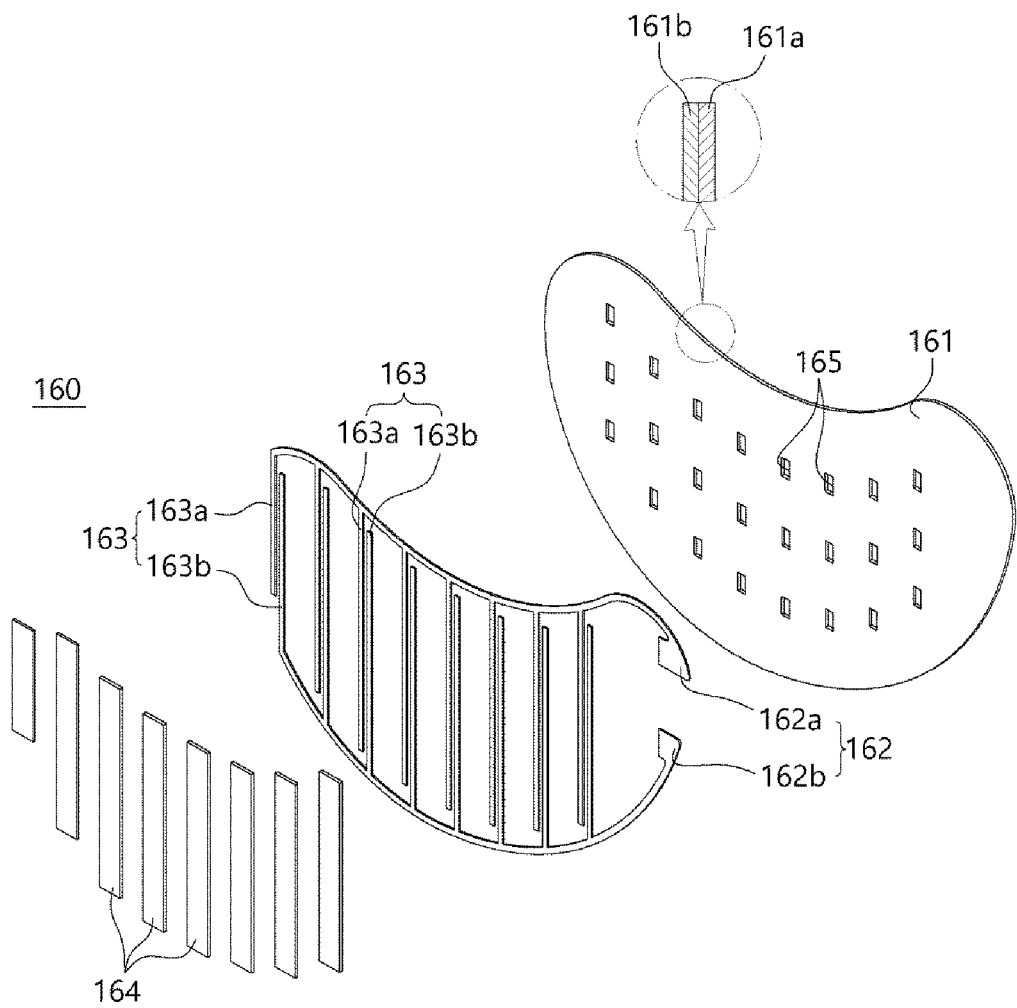
FIG. 12 is an exploded view illustrating a detailed configuration of a heat generation part in FIG. 10.

To this end, as shown in FIG. 12, the heat generation part 160 may include a base substrate 161, a lead electrode part 162, a branch electrode part 163, and a conductive heat generation material 164.

The base substrate 161 may be provided in a plate shape having a predetermined area.

Such a base substrate 161 may support the lead electrode part 162 and the branch electrode part 163 which are formed on at least one surface thereof and may block the lead electrode part 162 and the branch electrode part 163 from being electrically connected to the light source part 110'.

In addition, the base substrate 161 may be made of a material having flexibility and pliability. Accordingly, even when the base substrate 161 is crumpled or bent by an external force, it is possible to prevent cracks from occurring in the lead electrode part 162 and the branch electrode part 163.

To this end, as shown in FIG. 12, the base substrate 161 may include a film member 161a having an insulating property and a porous substrate 161b stacked on one surface of the film member 161a.

As an example, the film member 161a may be made of a polymer resin having an insulating property and flexibility, such as PU, PET, PP, PE, or PVDF, and the porous substrate 161b may be cloth, a fabric, a nonwoven fabric, a porous film, a membrane, or the like.

As a specific example, the film member 161a may be a PU film, and the base substrate 161 may be a nanofiber web in which nanofibers including a synthetic polymer are accumulated in a three-dimensional network structure so as to have pores.

In this case, when the lead electrode part 162 and the branch electrode part 163 are formed on the porous substrate 161b through a printing method using a conductive paste, the conductive paste may fill the pores. Accordingly, the base substrate 161 may serve as a circuit board on which the lead electrode part 162 and the branch electrode part 163 are patterned and formed through the porous substrate 161b.

As a non-limiting example, the porous substrate 161b may be a single-layered or multi-layered nanofiber web in which a spinning solution prepared by mixing a synthetic polymer and a solvent is electrospun and accumulated to have pores.

Accordingly, since the porous substrate 161b is implemented in the form of a nanofiber web through a synthetic polymer having elasticity and pliability, the porous substrate 161b can secure elasticity and pliability.

As described above, the lead electrode part 162 and the branch electrode part 163 may be formed in a predetermined pattern on at least one surface of the porous substrate 161b and may provide a conduction path through which a current flows when power is applied.

The lead electrode part 162 and the branch electrode part 163 may be formed in a predetermined pattern on one surface of the porous substrate 161b through various known methods such as a plating method, an etching method, and a printing method using a conductive material.

As an example, the lead electrode part 162 and the branch electrode part 163 may be formed on the porous substrate 161b through a printing method using a conductive paste. Here, the conductive paste may be an Ag paste but is not limited thereto, and any known conductive paste used to constitute an electrode may be used.

In this case, the lead electrode part 162 and the branch electrode part 163 may be electrically conducted to each other through the conductive heat generation material 164 when power is applied.

As a specific example, as shown in FIGS. 10 and 12, the lead electrode part 162 may include two lead electrodes 162a and 162b which are formed along an edge of one surface of the base substrate 161 and are not physically connected to each other.

In addition, the branch electrode part 163 may include two branch electrodes 163a and 163b which extend from the two lead electrodes 162a and 162b so as to not be electrically connected to each other and to have partially overlapping lengths.

That is, the lead electrode part 162 may include a first lead electrode 162a and a second lead electrode 162b, the branch electrode part 163 may include a first branch electrode 163a extending from the first lead electrode 162a and a second branch electrode 163b extending from the second lead electrode 162b, and the first branch electrode 163a and the second branch electrode 163b may be disposed such that partial lengths of entire lengths thereof face each other.

In this case, the conductive heat generation material 164 may be formed on one surface of the base substrate 161 so as to cover an area of facing portions of the first branch electrode 163a and the second branch electrode 163b.

That is, the conductive heat generation material 164 may be formed to have an area including a partial or entire area of the facing portions of the first branch electrode 163a and the second branch electrode 163b.

Accordingly, the conductive heat generation material 164 may be formed to be in direct contact with the first branch electrode 163a and the second branch electrode 163b and to fill the area of the facing portions between the first branch electrode 163a and the second branch electrode 163b.

In this case, the branch electrode part 163 may be provided as a plurality of branch electrode parts 163, and the plurality of branch electrode parts 163 may be spaced apart from each other by a predetermined interval along a length direction of the lead electrode part 162.

That is, a plurality of first branch electrodes 163a may each extend from the first lead electrode 162a so as to be spaced apart from each other by a predetermined interval along a length direction of the first lead electrode 162a, and a plurality of second branch electrodes 163b may each extend from the second lead electrode 162b to be spaced apart from each other by a predetermined interval along a length direction of the second lead electrode 162b.

In addition, the plurality of first branch electrodes 163a and the plurality of second branch electrodes 163b may be formed to be alternately arranged along the length direction of the lead electrode part 162.

Accordingly, the plurality of branch electrode parts 163 may be spaced apart from each other by a predetermined interval along the length direction of the lead electrode part 162.

In this case, the conductive heat generation material 164 may also be provided as a plurality of conductive heat generation materials 164, and the plurality of conductive heat generation materials 164 may be formed on one surface of the base substrate 161 to each connect the two first and second branch electrodes 163a and 163b which are paired with each other.

Accordingly, when power is supplied, the conductive heat generation material 164 may generate heat while electrically conducting the first branch electrode 163a and the second branch electrode 163b which are paired with each other.

Accordingly, the LED patch 200 for a skin care apparatus according to the present embodiment may implement a heating function through heat generated by the heat generation part 160 when power is supplied.

For this reason, it is possible to promote the penetration of active ingredients into the user's skin, thereby enhancing an effect of improving skin beauty through the active ingredients. In addition, it is possible to transfer heat to the user's skin, thereby assisting in activating skin collagen, and it is possible to open pores, thereby inducing the discharge of unnecessary wastes.

Figure 13:
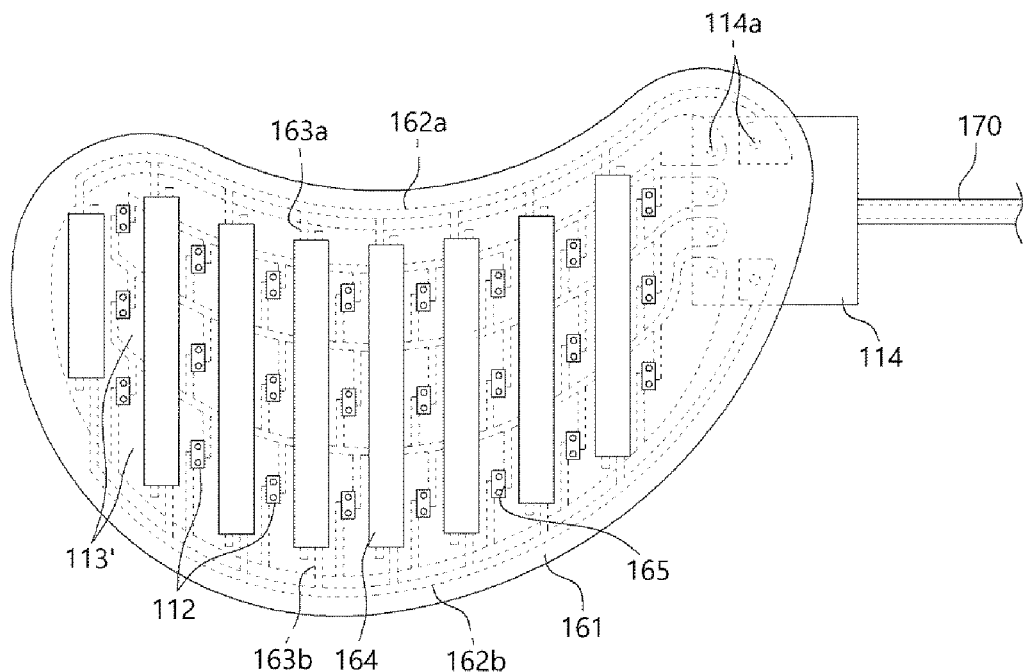
FIG. 13 is a plan view illustrating a state in which a cover part is removed in FIG. 9.

In this case, in a case in which the plurality of branch electrode parts 163 and the plurality of conductive heat generation materials 164 are provided, as shown in FIG. 13, the plurality of branch electrode parts 163 and the plurality of conductive heat generation materials 164 may be disposed to be located at positions that do not overlap the LEDs 112 provided in the light source part.

Accordingly, the LED 112 of the light source part may be disposed between conductive heat generation materials 164 without overlapping the conductive heat generation materials 164 constituting the heat generation part 160.

Accordingly, light generated from the LED 112 can be smoothly irradiated toward the user's skin without being blocked by the conductive heat generation material 164, and the LED 112 can minimize heat generated from the conductive heat generation material 164 being transferred toward the LED 112.

For this reason, even when the LED patch 200 for a skin care apparatus according to the present embodiment includes both the light source part 110 or 110' for a skin improvement effect using light and the heat generation part 160 for a heating function, both the light source part 110 or 110' and the heat generation part 160 can operate smoothly.

In this case, the base substrate 161 may include arrangement holes 165 formed to pass through regions corresponding to the LEDs 112, and when the heat generation part 160 is disposed on one surface of the light source part 110 or 110', the LED 112 may be disposed to the arrangement hole 165 side.

Here, when the first cover member 121 includes the arrangement hole 116, the arrangement hole 116 formed in the first cover member 121 and the arrangement hole 165 formed in the base substrate 161 may be formed at positions corresponding to each other.

Accordingly, the LED 112 may be exposed to the outside through the arrangement hole 165 formed in the base substrate 161 and the arrangement hole 116 formed in the first cover member 121.

Meanwhile, the conductive heat generation material 164 may be a conductive constant temperature heat generation material so as to uniformly generate heat to a target temperature when power is supplied. Here, the conductive constant temperature heat generation material may be material that suppresses a heat-generating temperature through an increase in resistance when a temperature rises, and may be a known positive temperature coefficient, more specifically, a conductive carbon paste.

For this reason, when power is supplied and a heat-generating temperature of the heat generation part 160 reaches a target temperature, the conductive heat generation material 164 may block a flow of a current through an increase in resistance to electrically disconnect the first branch electrode 163*a* and the second branch electrode 163*b*, and when the heat-generating temperature of the heat generation part 160 is less than the target temperature, the conductive heat generation material 164 may allow a current to flow through a decrease in resistance to electrically connect the first branch electrode 163*a* and the second branch electrode 163*b*.

Accordingly, the heat generation part 160 can always generate a uniform temperature through such a process.

Here, although the heat generation part 160 is illustrated in drawings as being applied to the LED patch 100' for a skin care apparatus which is a type shown in FIGS. 5 to 8, the present invention is not limited thereto, and the heat generation part 160 may be equally applied to the LED patch 100 for a skin care apparatus which is a type shown in FIGS. 1 to 4.

Meanwhile, the LED patch 100, 100', or 200 for a skin care apparatus according to one embodiment of the present invention may include a circuit board 114 for supplying power toward the light source part 110 or 110' and/or the heat generation part 160.

For example, the circuit board 114 may be a known sub-printed circuit board (sub-PCB).

In this case, the circuit board 114 may be disposed on one surface of the substrate part 111, and the circuit board 114 may be disposed such that a partial area thereof overlaps the substrate part 111. Accordingly, the circuit board 114 may be electrically connected to the circuit pattern part 113 or 113' formed on the substrate part 111 and/or the lead electrode part 162 and the branch electrode part 163 of the heat generation part 160 through the via holes 114*a*.

Such a circuit board 114 may be electrically connected to a power supply for supplying power.

Accordingly, the light source part 110 or 110' and/or the heat generation part 160 may be driven using power supplied from the power supply through the circuit board 114.

In this case, in the LED patch 100, 100', or 200 for a skin care apparatus according to one embodiment of the present invention, driving power for driving the light source part 110 or 100' may be supplied from the outside.

To this end, the LED patch 100, 100', or 200 for a skin care apparatus according to one embodiment of the present invention may further include a connection cable 170 for electrical connection with an external power supply that is a power supply.

Figure 16:
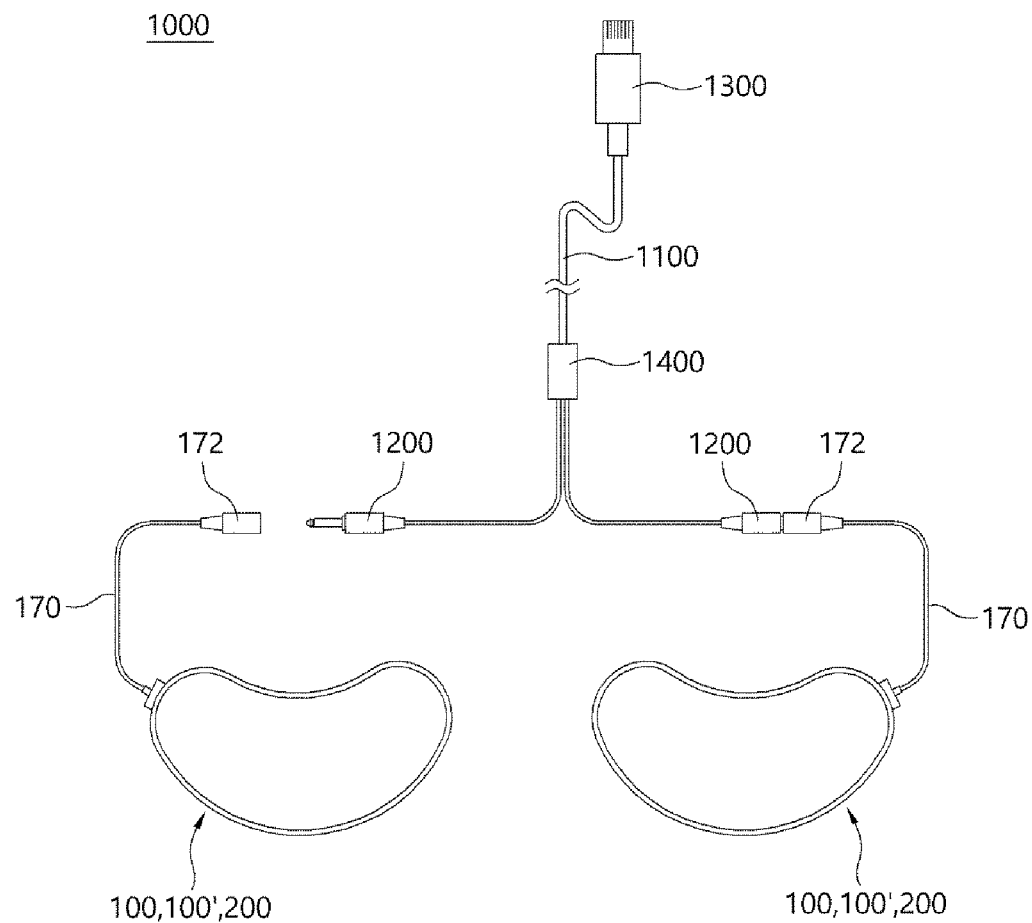
FIG. 16 is a schematic view illustrating a skin care apparatus according to one embodiment of the present invention.
Figure 17:
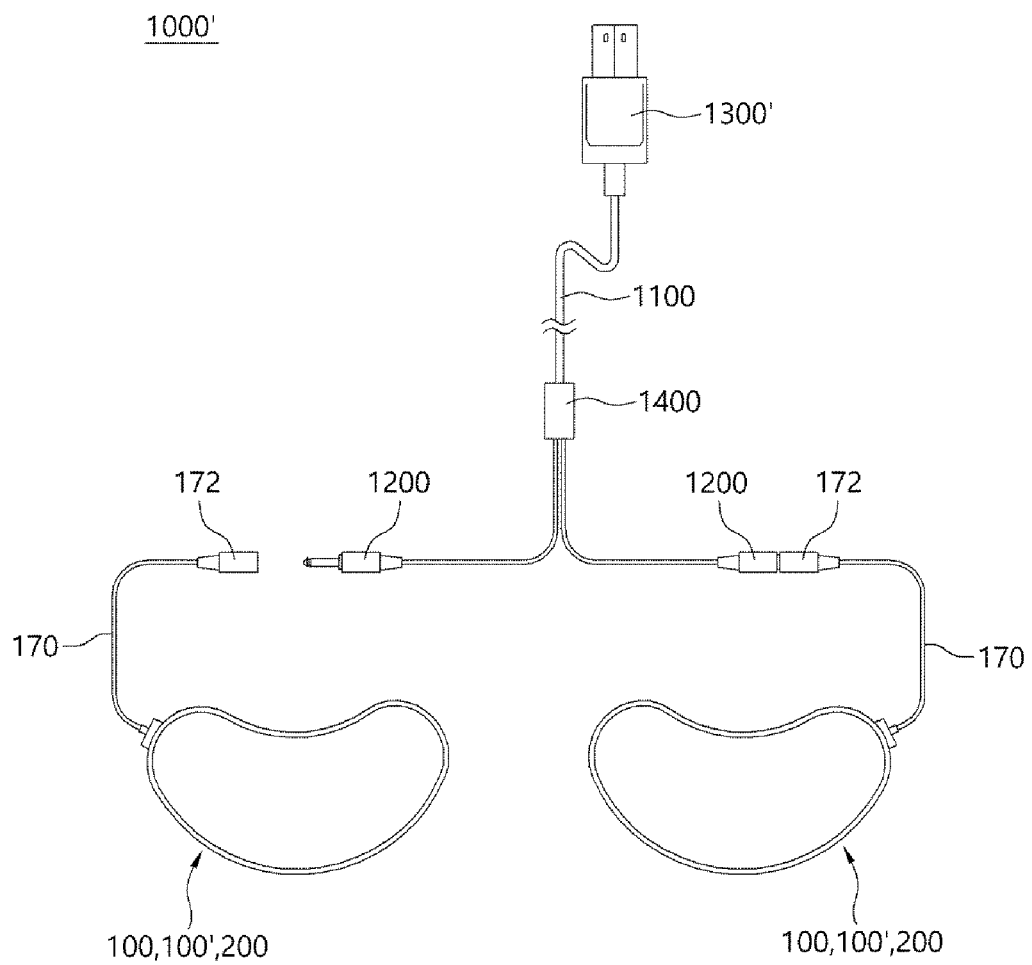
FIG. 17 is a view illustrating another type of connector in a skin care apparatus according to one embodiment of the present invention.

That is, as shown in FIGS. 16 and 17, the connection cable 170 may be provided with a connected port 172 to be connected at one end thereof so as to be connected to an external power supply device (not shown), and the other end thereof may be electrically connected to the circuit board 114.

Here, the connection cable 170 may be connected directly to the external power supply device or may be connected to the external power supply device through a separate member. In addition, the external power supply device may be a portable electronic device such as a mobile phone or an auxiliary battery.

Accordingly, the light source part 110 or 110' and/or the heat generation part 160 may be driven using power supplied from the external power supply device through the connection cable 170.

Alternatively, the LED patch 100, 100', or 200 for a skin care apparatus according to one embodiment of the present invention may be implemented in a type including a driving power source for driving the light source part 110 or 100'.

That is, a known battery (not shown) may be embedded in the LED patch 100, 100', or 200 for a skin care apparatus according to one embodiment of the present invention, and the battery may be electrically connected to the circuit board 114.

Accordingly, the light source part 110 or 110' and/or the heat generation part 160 may be driven using power supplied through the battery. In this case, a chipset such as a micro controller unit (MCU) for controlling overall driving may be mounted at the circuit board 114 side.

As described above, when the battery is embedded, after one surface of the first cover member 121 is attached directly to the user's skin, the LED patch 100, 100', or 200 for a skin care apparatus according to one embodiment of the present invention may operate independently.

Meanwhile, the LED patch 100, 100', or 200 for a skin care apparatus according to one embodiment of the present invention may have a shape including a portion having an irregular width in one direction as shown in FIGS. 1, 5, and 9.

As an example, the LED patch 100, 100', or 200 for a skin care apparatus according to one embodiment of the present invention may have a shape of which one side is concave inward and may have a shape similar to that of an eyebrow.

In addition, the LED patch 100, 100', 200 for a skin care apparatus according to one embodiment of the present invention may have various other shapes such as a circular shape and an arc shape excluding shapes with a constant width along a length direction thereof, such as a rectangular shape or a square shape, or a polygonal shape excluding a rectangular shape.

However, the overall shape of the LED patch 100, 100', or 200 for a skin care apparatus according to one embodiment of the present invention is not limited thereto, and the LED patch 100, 100', 200 for a skin care apparatus according to one embodiment of the present invention may have a rectangular shape having a constant width along a length direction thereof.

The LED patch 100, 100', 200 for a skin care apparatus according to one embodiment of the present invention as described above may be implemented as a skin care apparatus 1000 or 1000' for emitting light for skin improvement to user' skin or providing heat as well as the light for skin improvement in a state in which the LED patch 100, 100', or 200 for a skin care apparatus is attached to a part of a body.

Accordingly, a user can obtain a skin improvement effect using light irradiated from the LED 112 when power is supplied from the outside in a state in which the LED patch 100, 100', or 200 for a skin care apparatus is attached to the user's skin. In addition, when the LED patch 100, 100', or 200 for a skin care apparatus includes a heat generation part 160, it is possible to promote the penetration of active ingredients using heat provided from the heat generation part 160.

As an example, as shown in FIGS. 16 and 17, the skin care apparatus 1000 or 1000' may include at least one of the LED patches 100, 100', and 200 for a skin care apparatus described above, and include a connection part 1100 for electrically connecting the LED patch 100, 100', or 200 for a skin care apparatus to a power supply device.

Here, the at least one of the LED patches 100, 100', or 200 for a skin care apparatus may be a type including a connection cable 170.

In addition, the skin care apparatus 1000 or 1000' may include two of the LED patches 100, 100', and 200 for a skin care apparatus each including the connection cable 170, and two of the LED patches 100, 100', and 200 for a skin care apparatus may be connected to the power supply device through one connection part 1100.

Specifically, the connection part 1100 may include one or more connection ports 1200 electrically connected to the LED patches 100, 100', and 200 for a skin care apparatus and a connector 1300 or 1300' electrically connected to the power supply device.

As an example, the connection part 1100 may include two connection ports 1200 electrically connected to the connection cables 170 included in the LED patches 100, 100', and 200 for a skin care apparatus.

Accordingly, in the connection part 1100, the two connection ports 1200 may be electrically connected to the connected ports 172 to be connected of two of the LED patches 100, 100', and 200 for a skin care apparatus, and the connector 1300 or 1300' may be connected to an external power supply device such as a known auxiliary battery.

Accordingly, in the skin care apparatuses 1000 and 1000' according to one embodiment of the present invention, power may be supplied to the LED patches 100, 100', and 200 for a skin care apparatus from the external power supply device such as the auxiliary battery through the connection part 1100.

In addition, when the external power supply device is a portable auxiliary battery or a portable electronic device, the skin care apparatus 1000 or 1000' according to one embodiment of the present invention can be used without restriction on movement in a state in which the portable auxiliary battery or the portable electronic device is possessed or carried.

In the present embodiment, the connectors 1300 and 1300' may be appropriately changed according to types of the external power supply device.

For example, as shown in FIG. 16, the connector 1300 may be a micro 5-pin, 8-pin, or C-type connector so as to be connected to a portable electronic device, and as shown in FIG. 17, the connector 1300' may be a universal serial bus (USB) connector connected to a known auxiliary battery.

In this case, the skin care apparatus 1000 or 1000' according to one embodiment of the present invention may further include a control part 1400 for controlling an overall operation.

For example, the control part 1400 may be implemented as a remote control type control box that can be operated by the user and may be provided at the connection part 1100 side.

In addition, the control part 1400 may include a controller such as an MCU to control overall operations of the skin care apparatuses 1000 and 1000'.

As an example, the control part 1400 may control various functions such as an on/off function of a light source part 110 or 110', a selection or change function of an emission mode of the light source part, an automatic-off function after a predetermined time has elapsed, an on/off function of a heat generation part 160, and a selective driving function of the light source part 110 or 110' and the heat generation part 160.

Accordingly, the control part 1400 may control overall operations of the LED patches 100, 100', and 200 for a skin care apparatus.

In addition, when the LED patch 100, 100', or 200 for a skin care apparatus includes the above-described temperature sensor 115, the control part 1400 may control the on/off of the light source part 110 or 110' and/or the driving of the heat generation part 160 based on temperature information transmitted from the temperature sensor 115.

Accordingly, the skin care apparatuses 1000 and 1000' according to one embodiment of the present invention may prevent the light source parts 110 and 110' and/or the heat generation part 160 from operating at a high temperature, thereby protecting the user from being burned due to the high temperature in advance.

In addition, the temperature sensor 115 may be mounted on the control part 1400 side instead of being mounted at the light source part 110 or 100' side of the LED patch 100, 100', or 200 for a skin care apparatus.

While the embodiments of the present invention have been described above, the present invention is not limited to the embodiment presented herein. One skilled in the art may easily suggest other embodiments due to addition, modification, deletion, and the like of components within the scope and spirit of the present invention, and the addition, modification, deletion, and the like of the components fall within the scope and spirit of the present invention.

The invention claimed is:

1. A light-emitting diode (LED) patch for a skin care apparatus, comprising:
    a substrate part;
    a circuit pattern part formed in at least two layers on the substrate part;
    a light source part including one or more LEDs mounted directly on the circuit pattern part; and
    a cover part configured to cover at least one surface of the substrate part,
    wherein the circuit pattern part includes:
    a first pattern formed directly on the substrate part, wherein the first pattern has a pattern shape; and
    a second pattern having the same pattern shape and attached to one surface of the first pattern through a conductive adhesive layer,
    wherein the first pattern is a printed pattern formed directly on the substrate part and configured to fill pores of the substrate part with a conductive material,
    wherein the second pattern is stacked on one surface of the first pattern through the conductive adhesive layer so that it is located directly on an upper surface of the first pattern, and
    wherein the first pattern and the second pattern secure conductive stability for the one or more LEDs by compensating for mutual short circuits.

2. The LED patch of claim 1, wherein:
    the printed pattern is formed by filling the pores formed in the substrate part with the conductive material; and
    the second pattern is a conductive microfiber web in which a microfiber web is plated with a conductive material.

3. The LED patch of claim 1, wherein:
    the circuit pattern part includes a plurality of patterns which are not electrically connected to each other; and
    the plurality of patterns are electrically connected to each other through the one or more LEDs mounted directly on the circuit pattern part.

4. The LED patch of claim 3, wherein the plurality of patterns electrically connected to each other through the one or more LEDs are linear patterns or planar patterns having a predetermined area.

5. The LED patch of claim 1, wherein:
the cover part includes a first cover member and a second cover member which are disposed on both surfaces of the substrate part, respectively, such that the first cover member covers the one or more LEDs; and
the first cover member covering the one or more LEDs is a light-transmitting member, and the second cover member is a translucent member or an opaque member.

6. The LED patch of claim 5, wherein the first cover member includes a light diffusion material.

7. The LED patch of claim 1, further comprising a support sheet having a plate shape which is disposed on a surface opposite to the one surface of the substrate part, on which the circuit pattern part is formed and supports the substrate part.

8. The LED patch of claim 7, further comprising a heat dissipation sheet disposed on a surface of the support sheet.

9. The LED patch of claim 1, further comprising a protective layer formed on an exposed surface of the cover part.

10. The LED patch of claim 1, further comprising one or more temperature sensors.

11. The LED patch of claim 1, further comprising a heat generation part configured to generate heat when power is applied.

12. The LED patch of claim 11, wherein the heat generation part includes:
a base substrate having a plate shape;
a lead electrode part formed along an edge of one surface of the base substrate and including lead electrodes which are not physically connected to each other;
a branch electrode part including branch electrodes which are not electrically connected to each other and which each extend from the lead electrode part such that partial lengths of the branch electrodes face each other; and
a conductive heat generation material which has a predetermined area, is formed to be located at overlapping portions of the branch electrodes, and generates heat while electrically conducting the branch electrodes when power is supplied.

13. The LED patch of claim 12, wherein:
the heat generation part includes a plurality of branch electrode parts spaced apart from each other by a predetermined interval along a length direction of the lead electrode part, and a plurality of conductive heat generation materials provided at each of the plurality of branch electrode parts; and
the plurality of branch electrode parts and the plurality of conductive heat generation materials are disposed to be located at positions that do not overlap the plurality of LEDs.

14. The LED patch of claim 12, wherein:
the base substrate includes a film member having an insulating property, and a porous substrate stacked on one surface of the film member; and
the lead electrode part and the branch electrode part are formed on the porous substrate.

15. The LED patch of claim 1, further comprising a connection cable configured to supply power supplied from an outside toward the light source part.

16. The LED patch of claim 15, wherein the connection cable is electrically connected to the light source part through a circuit board disposed such that a partial area thereof overlaps the substrate part.

17. The LED patch of claim 15, wherein the connection cable includes a connected port to be connected provided at one end thereof so as to be connected to an external power supply device.

18. A skin care apparatus comprising:
at least one LED patch for a skin care apparatus of claim 1;
a connection part configured to electrically connect an external power supply device and a connection cable of the at least one LED patch for a skin care apparatus to each other; and
a control part provided in the connection part to control overall driving of the light source part.

19. The skin care apparatus of claim 18, wherein the external power supply device is a portable electronic device or an auxiliary battery.

\* \* \* \* \*